US00PP27195P2

(12) United States Plant Patent
Shim

(10) Patent No.: US PP27,195 P2
(45) Date of Patent: Sep. 27, 2016

(54) ***HIBISCUS* PLANT NAMED 'SHIMRR38'**

(50) Latin Name: *Hibiscus syriacus*
Varietal Denomination: SHIMRR38

(71) Applicant: Kyung Ku Shim, Cheonan-si (KR)

(72) Inventor: Kyung Ku Shim, Cheonan-si (KR)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/545,051

(22) Filed: Mar. 19, 2015

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hibiscus* plant named 'SHIMRR38', characterized by its relatively compact, upright to outwardly spreading plant habit; vigorous and uniform growth habit; flowers with reddish purple-colored petals with dark red-colored centers; and good garden performance.

2 Drawing Sheets

Botanical designation: *Hibiscus syriacus*.
Cultivar denomination: 'SHIMRR38'.

BACKGROUND OF THE INVENTION

The present invention relates to a new and distinct cultivar of *Hibiscus* plant, botanically known as *Hibiscus syriacus*, commercially known as Rose-of-Sharon or Althea, and hereinafter referred to by the cultivar name 'SHIMRR38'.

The new *Hibiscus* plant is a product of a planned breeding program conducted by the Inventor in Suwon-si, Gyeonggi-do, Korea. The objective of the breeding program was to develop new *Hibiscus* plants with attractive flower forms and colors.

The new *Hibiscus* plant originated from a cross-pollination conducted by the Inventor in July, 2001 of *Hibiscus syriacus* 'SKK 14-1-15', not patented, as the female, or seed, parent with *Hibiscus syriacus* 'Songam', not patented, as the male, or pollen, parent. The new *Hibiscus* plant was discovered and selected by the Inventor in August, 2003 as a single flowering plant within the progeny of the stated cross-pollination in a controlled environment in Suwon-si, Gyeonggi-do, Korea.

Asexual reproduction of the new *Hibiscus* plant by softwood cuttings since March, 2004 in a controlled environment in Suwon-si, Gyeonggi-do, Korea has shown that the unique features of this new *Hibiscus* plant are stable and reproduced true to type in successive generations of asexual reproduction.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SHIMRR38'. These characteristics in combination distinguish 'SHIMRR38' as a new and distinct *Hibiscus* plant:

1. Relatively compact, upright to outwardly spreading plant habit.
2. Vigorous and uniform growth habit.
3. Flowers with reddish purple-colored petals with dark red-colored centers.
4. Good garden performance.

Plants of the new *Hibiscus* can be compared to plants of the female parent, 'SKK 14-1-15'. Plants of the new *Hibiscus* differ primarily from plants of 'SKK 14-1-15' in flower color as flowers of plants of 'SKK 14-1-15' have pink-colored petals.

Plants of the new *Hibiscus* can be compared to plants of the male parent, 'Songam'. Plants of the new *Hibiscus* differ primarily from plants of 'Songam' in plant size as plants of the new *Hibiscus* are more compact than plants of 'Songam'.

Plants of the new *Hibiscus* can be compared to plants of the *Hibiscus syriacus* 'Woodbridge', not patented. In side-by-side comparisons conducted in Grand Haven, Mich., plants of the new *Hibiscus* differed from plants of 'Woodbridge' in the following characteristics:

1. Plants of the new *Hibiscus* were more compact than plants of 'Woodbridge'.
2. Plants of the new *Hibiscus* and 'Woodbridge' differed in flower color as plants of 'Woodbridge' had flowers with fuchsia pink-colored petals with dark pink-colored centers.

Plants of the new *Hibiscus* can also be compared to plants of the *Hibiscus syriacus* 'SHIMRV24', disclosed in U.S. Plant Pat. No. 26,374. In side-by-side comparisons conducted in Grand Haven, Mich., plants of the new *Hibiscus* differed from plants of 'SHIMRV24' in flower color as plants of 'SHIMRV24' had flowers with purple-colored petals with dark red purple-colored centers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet is a side perspective view of a typical plant of 'SHIMRR38' grown in a container.

The photograph on the second sheet is a close-up view of a typical flower of 'SHIMRR38'.

DETAILED BOTANICAL DESCRIPTION

The aforementioned photographs and following observations, measurements and values describe plants grown in three-gallon containers during the summer in a polypropylene-covered shadehouse in Grand Haven, Mich. and under cultural practices typical of commercial *Hibiscus* production. During the production of the plants, day temperatures ranged from 18° C. to 27° C. and night temperatures ranged from ranged from 5° C. to 10° C. Plants were two years old when the photographs and the description were taken. In the following detailed description, color references are made to The Royal Horticultural Society Colour Chart, 1995 Edition, except where general terms of ordinary dictionary significance are used.

Botanical classification: *Hibiscus syriacus* 'SHIMRR38'.

Parentage:

*Female, or seed, parent.*—*Hibiscus syriacus* 'SKK 14-1-15', not patented.

*Male, or pollen, parent.*—*Hibiscus syriacus* 'Songam', not patented.

Propagation:

*Type.*—By softwood cuttings.

*Time to initiate roots, summer.*—About 30 days at temperatures about 25° C. to 27C.

*Time to initiate roots, winter.*—About 60 days at temperatures about 20° C. to 22C.

*Time to produce a rooted young plant, summer.*—About 40 to 50 days at temperatures about 25° C. to 27C.

*Time to produce a rooted young plant, winter.*—About 60 to 70 days at temperatures about 20° C. to 22C.

*Root description.*—Fine; yellowish in color.

*Rooting habit.*—Freely branching; medium density.

Plant description:

*Plant and growth habit.*—Perennial shrub; relatively compact and upright to outwardly spreading plant habit; vigorous and uniform growth habit.

*Branching habit.*—Freely branching habit, usually about six primary branches with numerous secondary lateral branches developing per plant; pinching enhances lateral branch development.

*Plant height.*—About 60.5 cm.

*Plant diameter* (*area of spread*).—About 63 cm.

Lateral branch description:

*Length.*—About 23 cm.

*Diameter.*—About 3 mm.

*Internode length.*—About 4.5 cm.

*Aspect.*—About 30° to 45° from vertical.

*Strength.*—Strong, rigid.

*Texture, immature.*—Smooth, glabrous.

*Texture, mature.*—Woody.

*Color, immature.*—Close to 143A.

*Color, mature.*—Close to 199B.

Leaf description:

*Arrangement.*—Alternate, simple.

*Length.*—About 6.75 cm.

*Width.*—About 4.3 cm.

*Shape.*—Ovate.

*Apex.*—Acuminate.

*Base.*—Cuneate.

*Margin.*—Crenate, lobed.

*Texture, upper surface.*—Smooth, glabrous.

*Texture, lower surface.*—Pubescent.

*Venation pattern.*—Palmate.

*Color.*—Developing leaves, upper and lower surfaces: Close to 143A. Fully expanded leaves, upper surface: Close to 135A; venation, close to 138B. Fully expanded leaves, lower surface: Close to 138A; venation, close to 138B.

*Petioles.*—Length: About 1.4 cm. Diameter: About 1.3 mm. Texture, upper surface: Slightly pubescent. Texture, lower surface: Smooth, glabrous. Color, upper surface: Close to 137B. Color, lower surface: Close to 137A.

Flower description:

*Flower appearance and arrangement.*—Single rotate flowers; flowers terminal and axillary; freely flowering habit with usually about nine flowers developing per lateral branch; flowers face upright to mostly outwardly.

*Flower longevity.*—Flowers last for about two to three days on the plant; flowers not persistent.

*Natural flowering season.*—Plants of the new *Hibiscus* flower continuously from late spring to late summer in Michigan.

*Flower diameter.*—About 5.75 cm.

*Flower length* (*height*).—About 4.5 cm.

*Flower buds.*—Length: About 2.4 cm. Diameter: About 1.2 cm. Shape: Ovoid. Color: Close to 138B.

*Petals.*—Arrangement and quantity: Single whorl of five petals; petals imbricate. Length: About 5 cm. Width: About 2.9 cm. Shape: Obovate. Apex: Obtuse. Base: Attenuate. Margin: Entire; undulate. Texture, upper surface: Smooth, glabrous; satiny. Texture, lower surface: Slightly pubescent. Color: When opening, upper surface: Close to 76A; towards the base, close to 59A. When opening, lower surface: Close to 76D; towards the base, close to 58A. Fully opened, upper surface: Close to 73A; towards the base, close to 59C; at the base, close to 155D; venation, close to 73A and 59C; main color becoming closer to 76A with development. Fully opened, lower surface: Close to 73A; towards the base, close to 60A; venation, close to 73A and 60A; main color becoming closer to 76A with development.

*Sepals.*—Arrangement and quantity: Single whorl of six sepals fused into a tubular calyx. Length: About 1.2 cm. Width: About 2 mm. Shape: Narrowly deltoid. Apex: Narrowly acute. Base: Truncate. Margin: Entire. Texture, upper surface: Slightly pubescent; rough. Texture, lower surface: Smooth, glabrous. Color, when opening and fully opened, upper and lower surfaces: Close to 139B.

*Peduncles.*—Length: About 2 cm. Diameter: About 3 mm. Aspect: About 25° from stem axis. Strength: Strong; rigid. Texture: Slightly pubescent. Color: Close to 146A.

*Reproductive organs*.—Androecium: Quantity of stamens per flower: About 30. Filament length: About 4 mm. Filament color: Close to 155B. Anther shape: Round. Anther length: About 4 mm. Anther color: Close to 155A. Amount of pollen: Abundant. Pollen color: Close to 155A. Gynoecium: Quantity of pistils per flower: One. Pistil length: About 3.7 cm. Style length: About 3 cm. Style color: Close to 155C. Stigma appearance: Five-parted, rounded. Stigma color: Close to 155A. Ovary color: Close to 155C and 60B.

*Seeds and fruits*.—Seed and fruit development have not been observed on plants of the new *Hibiscus*.

Garden performance: Plants of the new *Hibiscus* have been observed to have excellent garden performance and to tolerate rain, wind, drought and temperatures ranging from about −12° C. to about 40° C.

Pathogen & pest resistance: Plants of the new *Hibiscus* have not been shown to be resistant to pathogens and pests common to *Hibiscus* plants.

It is claimed:

1. A new and distinct *Hibiscus* plant named 'SHIMRR38' as illustrated and described.

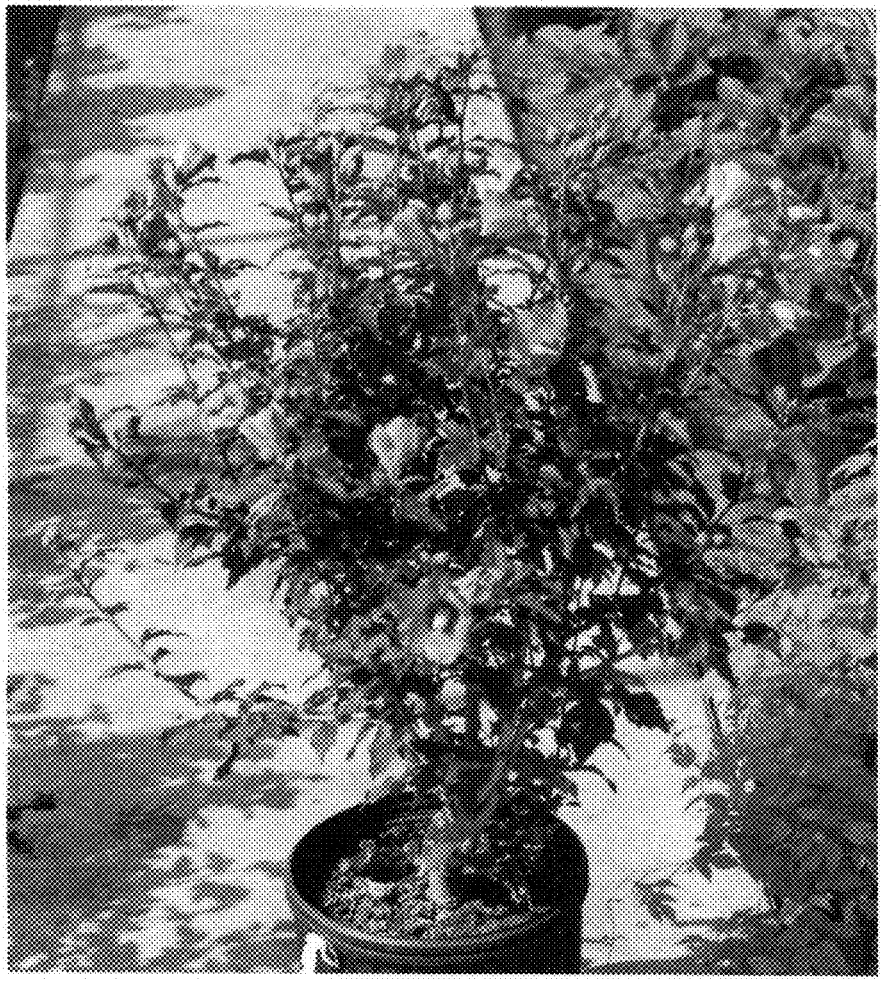

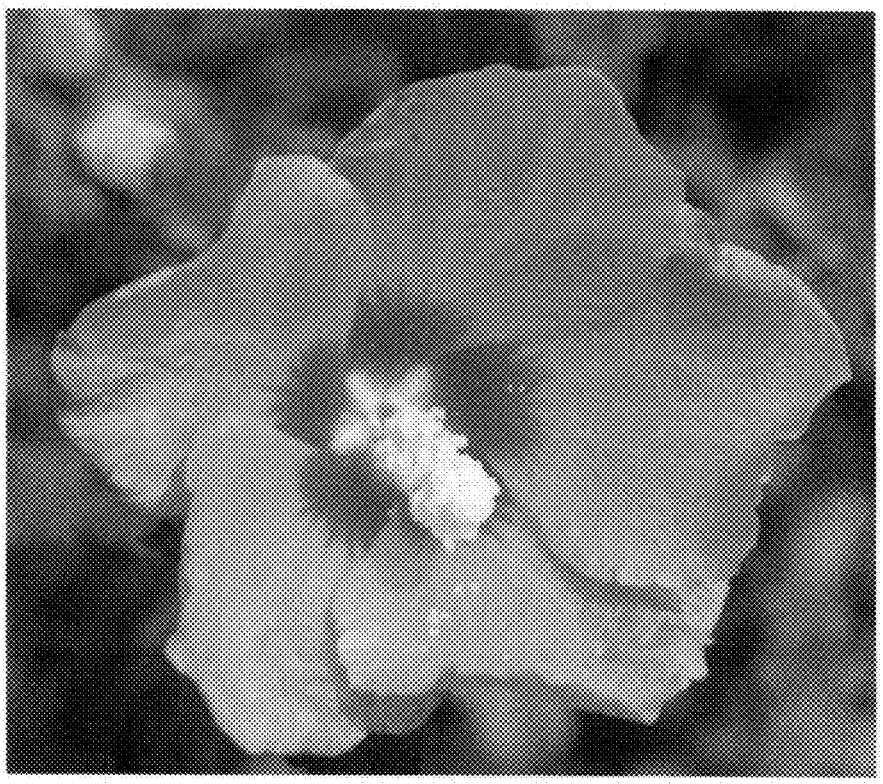

* * * * *